(12) United States Patent
Langerock et al.

(10) Patent No.: US 9,289,570 B2
(45) Date of Patent: Mar. 22, 2016

(54) BREATHING CIRCUIT SYSTEM

(75) Inventors: Rik Julia Raoul Langerock, Merelbeke (BE); Neil Anthony Kaye, New South Wales (AU); Malcolm Graham James, Halifax (GB); Jeno Kurja, Aerdenhout (NL)

(73) Assignee: PLASTIFLEX GROUP, Paal-Beringen (BE)

( * ) Notice: Subject to any disclaimer, the term of this patent is extended or adjusted under 35 U.S.C. 154(b) by 1057 days.

(21) Appl. No.: 13/318,712

(22) PCT Filed: May 5, 2010

(86) PCT No.: PCT/EP2010/056126
§ 371 (c)(1),
(2), (4) Date: Jun. 14, 2012

(87) PCT Pub. No.: WO2010/128089
PCT Pub. Date: Nov. 11, 2010

(65) Prior Publication Data
US 2012/0255550 A1 Oct. 11, 2012

(30) Foreign Application Priority Data

May 5, 2009 (EP) .................................. 09159435

(51) Int. Cl.
*F16K 31/02* (2006.01)
*A61M 16/10* (2006.01)
*A61M 16/08* (2006.01)
*A61M 16/16* (2006.01)

(52) U.S. Cl.
CPC ....... *A61M 16/1075* (2013.01); *A61M 16/1095* (2014.02); *A61M 16/0875* (2013.01); *A61M 16/16* (2013.01); *A61M 2205/3653* (2013.01); *A61M 2205/6027* (2013.01)

(58) Field of Classification Search
CPC ..................... A61M 16/1075; A61M 16/1095; A61M 16/0875; A61M 2205/3653; A61M 2205/6027; A61M 16/16; A45D 1/28; F24C 7/08; F24C 15/106; H05B 1/0213; H05B 3/56; H05B 3/58; Y10T 307/461; Y10T 307/469; Y10T 307/477; Y10T 307/484
USPC ............. 128/203.16–203.17, 203.26–203.27, 128/204.17
See application file for complete search history.

(56) References Cited

U.S. PATENT DOCUMENTS 5,988,164 A 11/1999 Paluch
7,061,252 B2* 6/2006 Bouton ............. A61M 16/1095
 128/203.17
7,120,354 B2* 10/2006 Mackie ................. A61M 16/08
 219/502

(Continued)

FOREIGN PATENT DOCUMENTS

DE 10 2007 003 455 A1 8/2008
WO 2005/028012 A1 3/2005
WO 2006/019323 A1 2/2006

*Primary Examiner* — Tan-Uyen (Jackie) T Ho
*Assistant Examiner* — Mark K Han
(74) *Attorney, Agent, or Firm* — Sughrue Mion, PLLC

(57) ABSTRACT

A breathing circuit system for supplying a breathable gas from a breathable gas supply system to a patient interface. The system comprises a heated conduit, comprising a hose and a hose heating system associated with the hose, and a plurality of adapter elements. The hose heating system is provided for operating within a first predetermined voltage range. A controller is associated with the breathing circuit and provides voltage within a second predetermined voltage range. Each adapter element comprises at least one electric component provided for adjusting the voltage supplied by the controller from a second range to the first range.

6 Claims, 1 Drawing Sheet

(56) References Cited

U.S. PATENT DOCUMENTS

| | | | |
|---|---|---|---|
| 8,063,343 B2* | 11/2011 | McGhin et al. | 219/497 |
| 9,119,933 B2* | 9/2015 | Bedford | A61M 16/06 |
| 2002/0083947 A1* | 7/2002 | Seakins | A61M 16/1075 128/204.17 |
| 2002/0112725 A1 | 8/2002 | Thudor et al. | |
| 2009/0107982 A1* | 4/2009 | McGhin et al. | 219/497 |

* cited by examiner

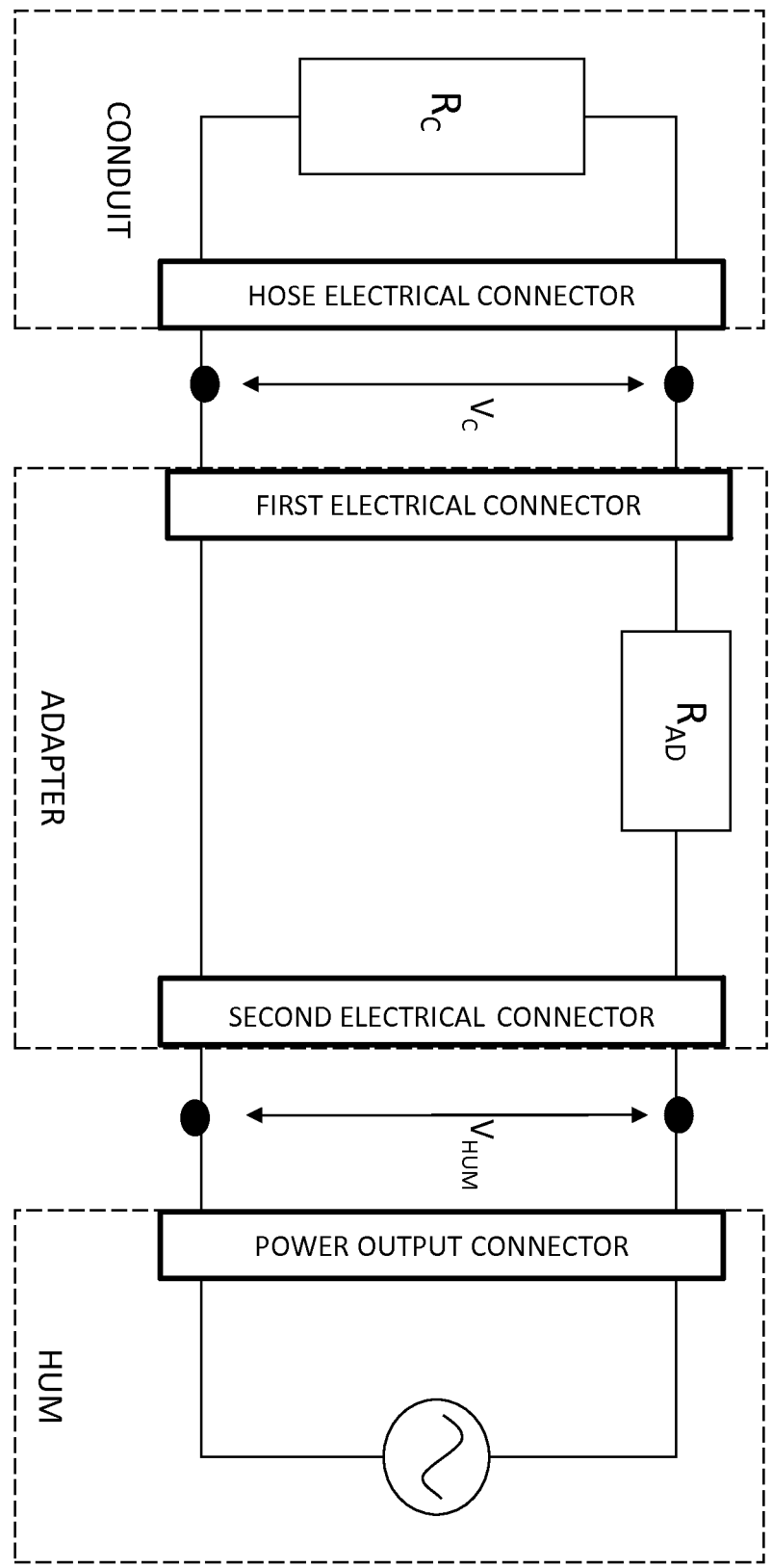

BREATHING CIRCUIT SYSTEM

TECHNICAL FIELD

The present invention relates to a breathing circuit system for use in a respiratory system for supplying a breathable gas from a breathable gas supply system to a patient interface, the breathing circuit system comprising a heated conduit, comprising a hose connectable between the air supply system and the patient interface and a hose heating system associated with the hose provided for heating the breathable gas travelling through the hose, the hose heating system being provided for operating within a first predetermined voltage range.

BACKGROUND ART

With the term 'breathable gas supply system' as used in this application is meant a system which is able to supply an amount of breathable gas to a patient, including, but not being limited thereto, a breathable gas supply system comprising a humidifier system, a stand alone humidifier, a flow generator (i.e. CPAP-machine, nPAP-machine, ventilator) with or without integrated humidifier, a nebulizer, an oxygen generator/concentrator with or without integrated humidifier, etc.

In breathable gas supply systems a breathable gas is delivered to a patient interface. In order to avoid side effects like dry nose, dry throat, to the patient, the air is often heated and humidified prior to being delivered to the patient. Conventional humidifier systems consist of warming water to an elevated temperature and passing an inspired air flow over or through the warm water to pick up the available humidity and equilibrate the resultant water vapor/air mixture to the humidifier temperature. The breathable gas is conducted to the patient through a hose. In order to reduce the risk of condensation within the hose, the hose usually comprises a hose heating element provided for heating the breathable gas, counteracting the heat lost along the length of the hose.

Today, during humidification of the breathable gas in respiratory systems, heated conduits are used which are specifically designed to operate with one type of humidifier only. In general, current heated conduits are designed to be used in combination with one specific breathable gas supply system only.

DISCLOSURE OF THE INVENTION

It is an aim of the invention to provide one generic type of heated conduit, i.e. a hose with an associated heating element, which can be used in combination with any type of breathable gas supply system.

Thereto, the breathing circuit system of the present invention comprises a plurality of adapter elements, each adapter element having a first electrical connector complementary to an electrical connector of the hose heating system and a second electrical connector complementary to a power output connector of a controller associated with the breathable gas supply system, the controller being provided for supplying voltage within a second predetermined voltage range to the hose heating element, each adapter element further comprising at least one electric component between the first and second electrical connectors having predetermined electric properties for adjusting the voltage supplied by the controller from the second range to the first range.

The second predetermined voltage range of the controller associated with the breathable gas supply system may differ for systems used for different applications, and even for the systems used for the same applications but made by different manufacturers. In fact, each controller of a breathable gas supply system operates within a system specific second predetermined voltage range. As an example, but not being limited thereto, a controller associated with a humidifier system may operate at a different voltage or within a different voltage range compared to a controller associated with a nebulizer system or a controller associated with a humidifier system of a first manufacturer may operate at a different voltage or within a different voltage range compared to a controller associated with a humidifier system of another second manufacturer.

In current breathable gas supply systems, the hose and the associated hose heating system are specifically designed to operate within the second predetermined voltage range of that specific breathable gas supply system. Thereto, the heated conduit has a certain fixed hose electrical resistance, which in combination with the second predetermined voltage range of the associated breathable gas supply system, is able to deliver the required heating energy to the breathable gas passing through the hose of the heated conduit. In order to be able to deliver the same amount of heating energy to the breathable gas, independent of the type of breathable gas supply system the heated conduit is connected to, and thus independent of the value of the second predetermined voltage range of the breathable gas supply system, the heated conduit needs to be replaced by another heated conduit with a different hose electrical resistance when changing the breathable gas supply system the heated conduit is connected to.

In order to solve this problem, the breathing circuit system according to the present invention comprises a plurality of adapter elements. The adapter element is provided between the controller associated with the breathable gas supply system and the heated conduit. The adapter element comprises an electric component with predetermined electric properties which is able to adjust the voltage supplied by the controller to the heated conduit from the second predetermined voltage range to a first predetermined voltage range. The first predetermined voltage range in combination with the hose electrical resistance determines the heating energy delivered to the breathable gas passing through the hose. When changing the breathable gas supply system, and thus when changing the second predetermined voltage range, the hose and associated hose heating system does not need to be changed. It is sufficient to change the adapter element with another adapter element, so as to change the voltage supplied to the hose heating system from the second predetermined voltage range to the first predetermined voltage range.

The breathing circuit system according to the invention is therefore able to use one standard heated conduit, a hose with an associated hose heating element, in combination with a number of adapter elements which are able to customize the system to any specific breathable gas supply system. As a result, the heated hose can be mass-customized and be made cheaper.

The at least one electric component of the adapter element can take any form considered suitable by the person skilled in the art. Preferably, the at least one electric component comprises an electrical resistance, which can be fixed or variable. Using a fixed resistance has the advantage that it reduces the risk to misuse and thus to a wrong adjustment between the second and first predetermined voltage range. Using a variable resistance has the advantage that one separate adapter element can be used for different specific second voltage range, i.e. in combination with several breathing circuit systems.

Optionally, the breathing circuit system may comprise associated sensing and/or communication elements. These sensors may for instance be incorporated into the conduit.

The controller associated with the breathable gas supply system can be incorporated in the breathable gas supply system or be an independent controller associated with the breathable gas supply system.

The invention will be further elucidated in the appended drawing.

FIG. 1 shows an electrical scheme of a preferred embodiment of a breathing circuit system according to the present invention.

The figure shows a breathing circuit system which comprises a heated conduit with a fixed resistance $R_C$. The heated conduit comprises a hose and an associated hose heating system provided for heating the breathable gas passing through the hose. The breathing circuit system shown in the figure further comprises an adapter element with a variable electrical resistance $R_{AD}$. The adapter element and the heated conduit are connected in series. The breathing circuit system is connected to a controller associated with a humidifier system, operating at a predetermined second voltage $V_{HUM}$. By changing the resistance of the adapter element $R_{AD}$, the current passing through the heated conduit $I_C$ can be adjusted. The current passing through the heated conduit $I_C$, together with the electrical resistance of the conduit $R_C$, determines the heating energy supplied to the breathable gas. This can be understood as follows:

$$V_{HUM} = V_C + V_{AD}$$
$$= I_C \times (R_C + R_{AD})$$

The resistance of the adapter element $R_{AD}$ can thus be chosen to adjust the voltage supplied by the humidifier to the heated conduit from the second predetermined voltage range to the first predetermined voltage range, i.e. from a voltage $V_{HUM}$ to a voltage $V_C$.

The invention claimed is:

1. A breathing circuit system for use in a respiratory system for supplying a breathable gas from a breathable gas supply system to a patient interface, the breathing circuit system comprising a heated conduit comprising:
    a hose connectable between the breathable gas supply system and the patient interface;
    a hose heating system associated with the hose provided for heating the breathable gas travelling through the hose, the hose heating system being provided for operating within a first predetermined voltage range; and
    a set of interchangeable adapter elements, each having different voltage determining characteristics for customising the hose to the breathable gas supply system, the adapter elements each having a first electrical connector complementary to and releasably connectable to an electrical connector of the hose heating system and a second electrical connector complementary to and releasably connectable to a power output connector of a controller associated with the breathable gas supply system, the controller being provided for supplying voltage within a second predetermined voltage range, the adapter elements each further comprising at least one electric component between the first and second electrical connectors having predetermined electric properties for adjusting the voltage supplied by the controller from the second range to the first range.

2. A breathing circuit system according to claim 1, characterized in that the at least one electric component comprises an electrical resistance.

3. A breathing circuit system according to claim 2, wherein the electrical resistance is a fixed resistance.

4. A breathing circuit system according to claim 2, wherein the electrical resistance is a variable resistance.

5. A breathing circuit system according to any one of claims 1-4, wherein the controller is incorporated in the breathable gas supply system.

6. A breathing circuit system according to any one of claims 1-4, the controller is an independent controller associated with the breathable gas supply system.

* * * * *